United States Patent
McLaughlin (10) Patent No.: US 10,029,097 B2
(45) Date of Patent: Jul. 24, 2018

(54) TARGETED CHANNEL SELECTION SYSTEMS AND METHODS

(71) Applicant: ADVANCED BIONICS AG, Staefa (CH)

(72) Inventor: Myles McLaughlin, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/531,799

(22) PCT Filed: Dec. 1, 2014

(86) PCT No.: PCT/US2014/067981
§ 371 (c)(1),
(2) Date: May 31, 2017

(87) PCT Pub. No.: WO2016/089359
PCT Pub. Date: Jun. 9, 2016

(65) Prior Publication Data
US 2017/0304619 A1    Oct. 26, 2017

(51) Int. Cl.
*A61N 1/36*    (2006.01)
*A61N 1/372*    (2006.01)
*A61N 1/05*    (2006.01)

(52) U.S. Cl.
CPC ....... *A61N 1/36038* (2017.08); *A61N 1/0541* (2013.01); *A61N 1/36034* (2017.08); *A61N 1/36039* (2017.08); *A61N 1/37247* (2013.01)

(58) Field of Classification Search
None
See application file for complete search history.

(56) References Cited

U.S. PATENT DOCUMENTS

| 3,449,768 A | * | 6/1969 | Doyle | A61F 9/08 600/25 |
| 6,289,247 B1 | | 9/2001 | Faltys et al. | |
| 7,120,500 B1 | * | 10/2006 | Seligman | A61N 1/378 607/55 |

(Continued)

FOREIGN PATENT DOCUMENTS

WO    WO-2012/123898    9/2012

OTHER PUBLICATIONS

International Search Report and Written Opinion received in International Application No. PCT/US14/067981, dated Jul. 31, 2015.

*Primary Examiner* — Kennedy Schaetzle
(74) *Attorney, Agent, or Firm* — ALG Intellectual Property, LLC (57) ABSTRACT

An exemplary targeted channel selection system may determine a target stimulation rate for a user of a cochlear implant system, determine a pulse width value that is representative of one or more pulse widths that are to be used for stimulation pulses applied by the cochlear implant system to the user during a stimulation session, and determine, based on the target stimulation rate and on the pulse width value, a value for N that is specific to the user. In this example, N represents a total number of analysis channels that are to be selected from M available analysis channels for presentation by the cochlear implant system to the user during a stimulation frame of the stimulation session.

20 Claims, 8 Drawing Sheets

(56) References Cited

U.S. PATENT DOCUMENTS

| | | | |
|---|---|---|---|
| 7,130,694 B1* | 10/2006 | Voelkel | A61N 1/36036 607/55 |
| 7,171,272 B2* | 1/2007 | Blamey | A61N 1/36036 607/57 |
| 7,251,530 B1* | 7/2007 | Overstreet | A61N 1/36036 607/137 |
| 7,317,944 B1 | 1/2008 | Overstreet | |
| 7,603,175 B2 | 10/2009 | Voelkel | |
| 8,000,797 B1 | 8/2011 | Sarpeshkar et al. | |
| 2010/0152813 A1* | 6/2010 | Lineaweaver | A61N 1/36032 607/57 |
| 2010/0280307 A1* | 11/2010 | Lineaweaver | A61N 1/36036 600/25 |
| 2011/0060385 A1 | 3/2011 | Lineaweaver | |
| 2012/0197065 A1* | 8/2012 | Botros | A61N 1/36032 600/25 |
| 2013/0272556 A1* | 10/2013 | Hamacher | H04R 25/305 381/328 |
| 2014/0079226 A1 | 3/2014 | Kludt et al. | |
| 2015/0367131 A1* | 12/2015 | Richter | A61N 1/36032 607/57 |

* cited by examiner

TARGETED CHANNEL SELECTION SYSTEMS AND METHODS

BACKGROUND INFORMATION

In a cochlear implant system with a total of M channels, the stimulation rate (i.e., the number of pulses per second that may be applied to a user of the cochlear implant system) on each individual channel can determine the amount of temporal information transferred over that channel. High stimulation rates can be good for transferring more temporal information to the user. However, stimulation rates beyond a certain maximum threshold may not result in the transfer of more temporal information and may actually waste power.

The loudness of one particular pulse is dependent on the amount of charge delivered, i.e., the pulse width or duration (measured in seconds) times the pulse amplitude (measured in amps). Therefore, to deliver sound at a most comfortable loudness level ("M level") associated with the user, with enough temporal information to support optimal sound quality, a cochlear implant may deliver high amplitude, short duration, pulses, which in turn supports high stimulation rates.

Unfortunately, generating high amplitude pulses requires a relatively high amount of power. To minimize power consumption, the cochlear implant may instead deliver low amplitude, long duration, pulses. While increasing the pulse duration may minimize power consumption, it may disadvantageously decrease the stimulation rate, which in turn may reduce the amount of temporal information that is transferred to the user.

One way to overcome this limitation is to use an N-of-M channel selection strategy in which a cochlear implant system only stimulates a subset of the available electrodes in each given stimulation frame. In an N-of-M channel selection strategy, a cochlear implant system divides an incoming audio signal into M analysis channels (or simply "channels") and then presents only N analysis channels to the user (e.g., by applying electrical stimulation representative of the signals contained within the N analysis channels by way of a plurality of intracochlear electrodes).

Because a number of channels are not selected (i.e., dropped) during each stimulation frame while a cochlear implant system operates in accordance with an N-of M channel selection strategy, the N-of M channel selection strategy may allow for a relatively high stimulation rate while at the same time minimizing power consumption. However, dropping channels may potentially result in some spectral information not being presented to the user, which in turn may lead to poor cochlear implant system performance. Thus, there is a tradeoff between preserving temporal information by keeping the stimulation rate high and preserving spectral information by keeping the value of N high.

Typically, N is arbitrarily set in a stimulation program, meaning that all cochlear implant users of that stimulation program will have the same number of channels selected for presentation during each stimulation frame. However, because each user has different M levels and pulse durations, fixing N across users can result in different stimulation rates for the users. For example, a fixed N for one user may result in a very low stimulation rate, which may lead to a loss of temporal information. This user may actually perform better with a lower N and a higher stimulation rate. For the same fixed N, another user may have a very high stimulation rate, beyond that needed to support good temporal information transfer. This user may actually benefit from having a higher N with improved spectral information transfer and a slightly lower stimulation rate that is still sufficient to support good temporal information transfer.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Targeted channel selection systems and methods are described herein. As will be described below, a targeted channel selection system may determine a target stimulation rate for a user of a cochlear implant system, determine a pulse width value that is representative of one or more pulse widths that are to be used for stimulation pulses applied by the cochlear implant system to the user during a stimulation session, and determine, based on the target stimulation rate and on the pulse width value, a value for N that is specific to the user. In this example, N represents a total number of analysis channels that are to be selected from M available analysis channels for presentation by the cochlear implant system to the user during a stimulation frame of the stimulation session.

The systems and methods described herein may allow for individualized values of N for different users (also referred to as "patients"). For example, first and second cochlear implant users may each be fitted with the same stimulation program (i.e., the same stimulation program may be loaded on to sound processor used by the first and second users). However, in accordance with the systems and methods described herein, a first value of N may be used within the stimulation program for the first user and as second value of N may be used within the stimulation program for the second user. This may allow each user to have a stimulation rate that is optimized to the user's needs and/or desires. In some instances, the systems and methods described herein may also facilitate low power consumption configurations without sacrificing temporal information being delivered to the user.

Figure 1:
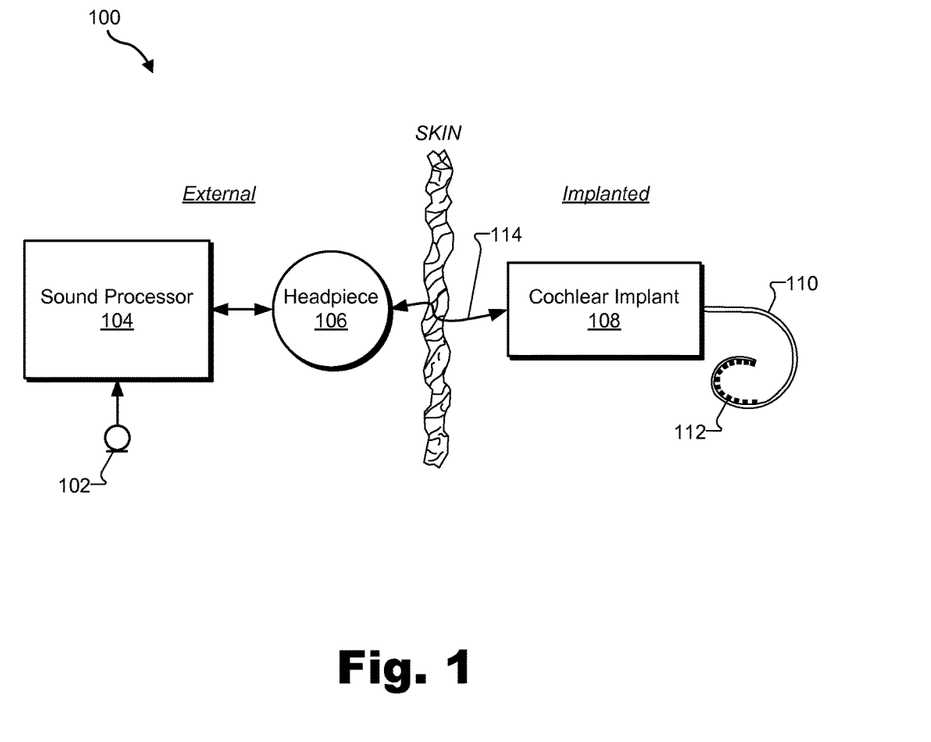
FIG. 1 illustrates an exemplary cochlear implant system according to principles described herein.

FIG. 1 illustrates an exemplary cochlear implant system 100. As shown, cochlear implant system 100 may include various components configured to be located external to a user including, but not limited to, a microphone 102, a sound processor 104, and a headpiece 106. Cochlear implant system 100 may further include various components configured to be implanted within the user including, but not limited to, a cochlear implant 108 and a lead 110 (also referred to as an intracochlear electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the user. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a user.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the user's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a user and configured to apply stimulation to one or more stimulation sites located along an auditory pathway of a user.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the user via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
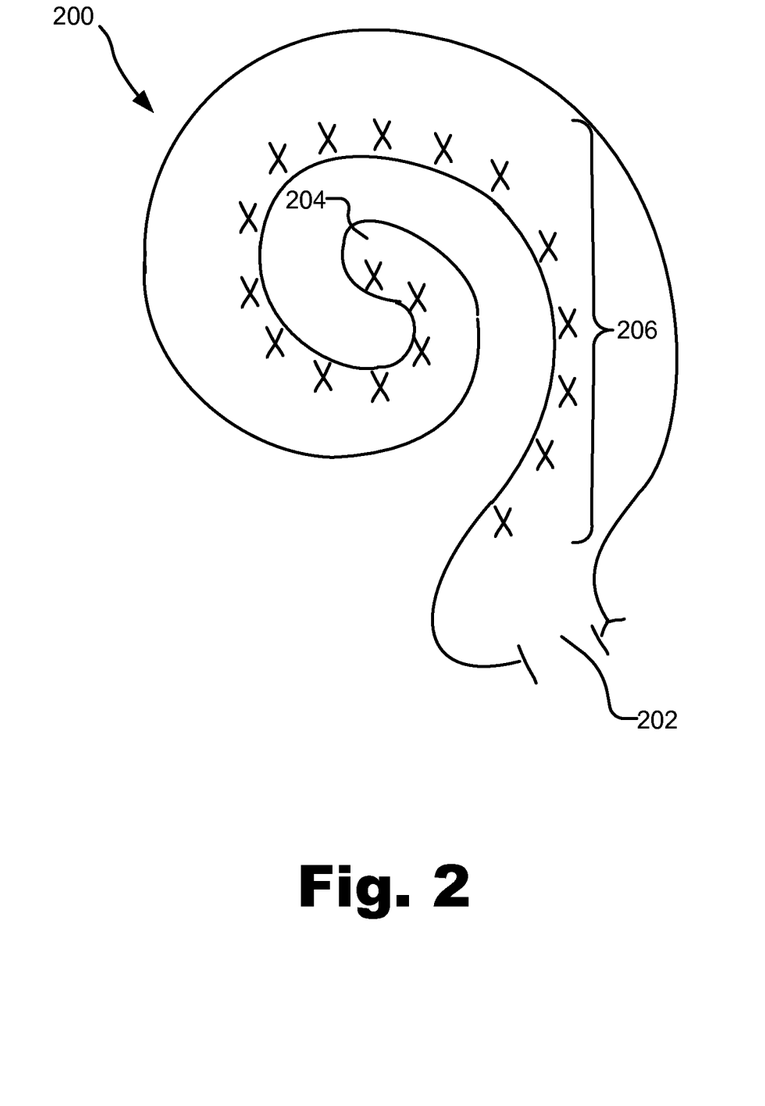
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

In some examples, a computing system separate from (i.e., not included within) cochlear implant system 100 may be selectively coupled to sound processor 104 in order to perform one or more fitting operations with respect to cochlear implant system 100, load one or more stimulation programs onto sound processor 104, and/or otherwise configure sound processor 104 as may serve a particular implementation.

Figure 3:
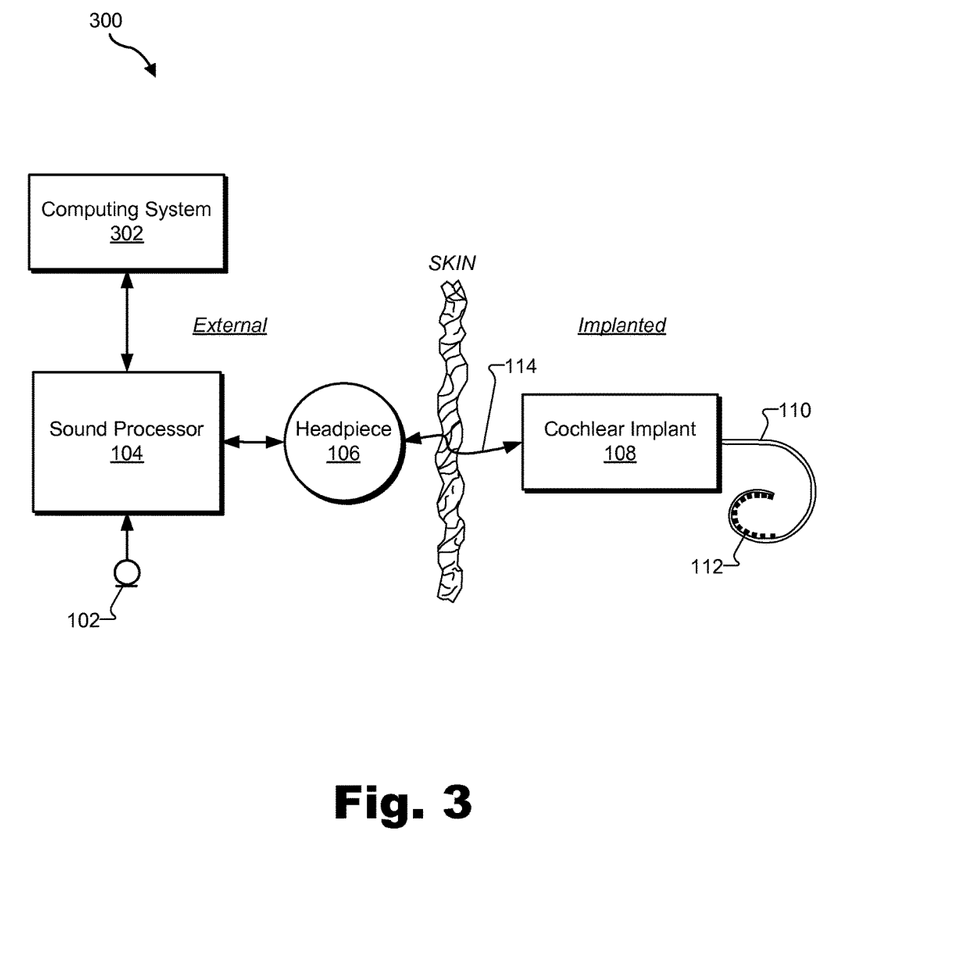
FIG. 3 shows an exemplary configuration in which a computing system is communicatively coupled to a sound processor according to principles described herein.

To illustrate, FIG. 3 shows an exemplary configuration 300 in which a computing system 302 is communicatively coupled to sound processor 104. Computing system 302 may be implemented by any suitable combination of computing and communication devices including, but not limited to, a fitting station or device, a programming device, a personal computer, a laptop computer, a handheld device, a mobile device (e.g., a mobile phone), a clinician's programming interface ("CPI") device, and/or any other suitable component as may serve a particular implementation. In some examples, computing system 302 may provide one or more graphical user interfaces ("GUIs") (e.g., by presenting the one or more GUIs by way of a display screen) with which a clinician or other user may interact.

In some examples, computing system 302 may be implemented by a fitting device configured to generate stimulation programs that may be loaded on to sound processor 104 for execution by sound processor 104. To this end, computing system 302 may be configured to receive user input (e.g., by way of a keyboard and/or other user input device). Computing system 302 may transmit data representative of stimulation programs, control parameters associated with the stimulation programs, and/or any other information to sound processor 104 in any suitable manner.

Figure 4:
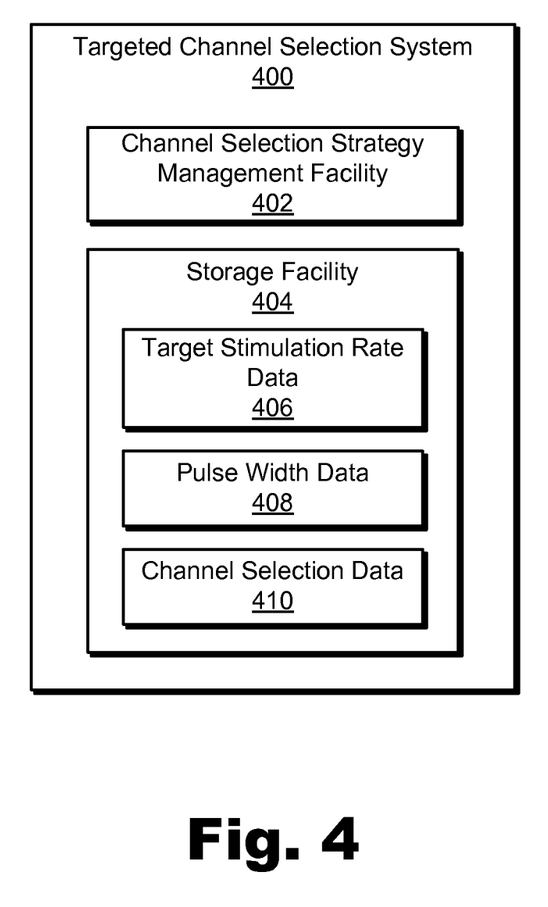
FIG. 4 illustrates an exemplary targeted channel selection system according to principles described herein.

FIG. 4 illustrates an exemplary targeted channel selection system 400 ("system 400"). System 400 may be configured to determine a value for N that is specific to a particular user and that may be used in an N-of-M channel selection strategy implemented by a cochlear implant system (e.g., cochlear implant system 100). System 400 may be implemented entirely by sound processor 104, entirely by computing system 302, or by a combination of sound processor 104 and computing system 302.

As shown, system 400 may include a channel selection strategy management facility 402 ("management facility 402") and a storage facility 404, which may be in communication with one another using any suitable communication technologies. Storage facility 404 may maintain target stimulation rate data 406 representative of one or more target stimulation rates, pulse width data 408 representative of one or more pulse width values, and channel selection data 410 representative of one or more values of N that are specific to one or more cochlear implant users. Storage facility 404 may maintain additional or alternative data as may serve a particular implementation. One or more of facilities 402 and 406 may be implemented by one or more processing devices (e.g., sound processor 104 and/or computing system 302) configured to perform one or more of the functions described herein.

Management facility 402 may perform various channel selection management operations. For example, management facility 402 may determine a target stimulation rate for a user of a cochlear implant system, determine a pulse width value that is representative of one or more pulse widths that are to be used for stimulation pulses applied by the cochlear implant system to the user during a stimulation session, and determine, based on the target stimulation rate and on the pulse width value, a value for N that is specific to the user. Each of these operations will be described in more detail below.

Management facility 402 may determine a target stimulation rate for a user of a cochlear implant system in any suitable manner. For example, management facility 402 may determine the target stimulation rate by receiving user input representative of the target stimulation rate. The user input may be provide by the user, by a clinician (e.g., a clinician involved in fitting the cochlear implant system to the user), and/or by any other user as may serve a particular implementation.

To illustrate, sound processor 104 of cochlear implant system 100 may be communicatively coupled to computing system 302, as illustrated in FIG. 3. In this configuration, computing system 302 may provide a graphical user interface for display on a display device included in or coupled to computing system 302. A user may provide user input representative of the target stimulation rate by way of the graphical user interface. Management facility 402 may receive the user input and set the target stimulation rate accordingly.

In some examples, the target stimulation rate may be set by a clinician or other user to be high enough to support good information transfer without using unnecessary stimulation pules. This may ensure that a low power program can be designed that preserves the same temporal information transfer present in a higher power program while achieving the maximum spectral information transfer possible for that user. In some examples, the target stimulation rate may be set based on the user's age. It is believed that slower stimulation rates may be better for older users. For example, a relatively old user may be assigned a relatively slow target stimulation rate, while a relatively young user may be assigned a relatively fast target stimulation rate.

Additionally or alternatively, management facility 402 may determine the target stimulation rate by identifying a stimulation rate used in a non-channel selection stimulation program for the user and designating the identified stimulation rate as the target stimulation rate. As used herein, a "stimulation program" refers to a manner in which a cochlear implant system processes and represents audio content presented to a cochlear implant user. A "non-channel selection stimulation program" refers to a stimulation program that does not employ an N-of-M channel selection strategy. In other words, a non-channel selection stimulation program directs a cochlear implant system to present each of the M available channels during each stimulation frame during a stimulation session in which the cochlear implant system operates in accordance with the non-channel selection stimulation program. In contrast, a "channel selection stimulation program" refers to a stimulation program that employs an N-of-M channel selection strategy.

To illustrate, the user may be used to a particular non-channel selection stimulation program (e.g., an "old" stimulation program that his or her cochlear implant system has executed for a relatively long period of time). The user may visit a clinic to upgrade to a new channel selection stimulation program. In order to facilitate a smooth transition between the old and new stimulation programs, management facility 402 may identify a stimulation rate used in the old stimulation program and designate the identified stimulation rate as the target stimulation rate that will be used for the new stimulation program. This identification may be performed by analyzing data representative of the old stimulation program and/or in any other suitable manner. It will be recognized that the old stimulation program may alternatively include a different type of channel selection stimulation program.

Additionally or alternatively, management facility 402 may determine the target stimulation rate by identifying a stimulation program that the user prefers, identifying a stimulation rate used in the identified stimulation program, and designating the identified stimulation rate as the target stimulation rate.

To illustrate, a plurality of stimulation programs may be loaded on sound processor 104. Sound processor 104 may switch between operating in accordance with each of the stimulation programs (e.g., automatically in response to a change in ambient environment of the user or manually in response to user actuation of a program switch). Over time, the user may develop a preference for a particular stimulation program. Management facility 402 may identify the preferred stimulation program in any suitable manner (e.g., by receiving user input representative of the particular stimulation program, determining that the particular stimulation program is used more than the other stimulation programs, etc.). Management facility 402 may analyze data representative of the preferred stimulation program to identify a stimulation rate used in the identified stimulation program and then designate the identified stimulation rate as the target stimulation rate. This analysis by management facility 402 may be performed automatically (e.g., as the user utilizes his or her cochlear implant system) or in response to user input.

Additionally or alternatively, management facility 402 may determine the target stimulation rate based on feedback provided by the user. For example, management facility 402 may use a plurality of different stimulation rates during a fitting session for the user, obtain feedback from the user with respect to the different stimulation rates, and designate, based on the feedback, a particular stimulation rate included in the plurality of different stimulation rates as the target stimulation rate. The obtained feedback may be subjective (e.g., the user may say that a particular stimulation rate sounds better than the others) or objective (e.g., in the form of measured evoked responses and/or speech recognition performance) as may serve a particular implementation.

Management facility 402 may determine a pulse width value that is representative of one or more pulse widths that are to be used for stimulation pulses applied by the cochlear implant system to the user during a stimulation session in any suitable manner. For example, management facility 402 may receive user input representative of the pulse width value (e.g., in any of the ways described herein).

In some examples, management facility 402 may determine the pulse width value based on an M level associated with the user and/or a power consumption requirement associated with the cochlear implant system. As used herein, an "M level" represents a most comfortable loudness level for a user. In order to achieve the M level, the total amount of charge included in a stimulation pulse must be at or above a certain threshold. Because the amount of charge depends on the stimulation amplitude and pulse width, the pulse width may be varied (e.g., increased) in order to achieve the most comfortable loudness level while still complying with a low power consumption requirement.

In some examples, the pulse width value determined by management facility 402 represents an actual pulse width of each of the stimulation pulses that are to be applied by the cochlear implant system to the user during a particular stimulation frame. In this scenario, the same pulse width is used for each of the stimulation pulses. In some alternative embodiments, stimulation pulses applied during a particular stimulation frame may have different pulse widths. In this scenario, the pulse width value determined by management facility 402 may represent an average pulse width of the stimulation pulses applied during the stimulation frame.

Once management facility 402 has determined the target stimulation rate and the pulse width value, management facility 402 may determine a value for N that is specific to the user. This may be performed in any suitable manner.

In some examples, management facility 402 may determine the value for N that is specific to the user in accordance with the following equation: $N_{value}=1/(PW*Rate_{target})$. In this equation, $N_{value}$ represents the value for N, PW represents the pulse width value, and $Rate_{target}$ represents the target stimulation rate.

For example, if the pulse width value determined by management facility 402 is 100 milliseconds and the target stimulation rate is 100 stimulation pulses per second, management facility 402 may determine that the value for N is ten. In this example, if M is sixteen, the N-of-M stimulation strategy may result in ten channels out of the sixteen available channels being selected for presentation to the user during each stimulation frame.

It will be recognized that management facility 402 may round up or down to obtain a whole number as may serve a particular implementation. For example, the equation above may yield a result of 8.7. In this case, management facility 402 may round up so that the determined value for N is 9.

In some examples, management facility 402 may ensure that the value for N does not go below a predetermined minimum value. For example, management facility 402 may determine the value for N in accordance with $N_{value}=\max(N_{min}, 1/(PW*Rate_{target}))$. In this equation, $N_{min}$ represents the predetermined minimum value for N. This has the effect of setting a minimum limit on the amount of spectral information a stimulation program that utilizes the value for N may preserve. In a low power channel selection program, this embodiment can determine the optimal N for preserving both temporal and spectral information for the user.

In some examples, once the value for N is determined, management 402 may generate or otherwise set a stimulation program that utilizes an N-of-M channel selection strategy (i.e., a stimulation program that directs the cochlear implant system to select only the N analysis channels from the M available analysis channels for presentation to the user during each stimulation frame while the cochlear implant system operates in accordance with the stimulation program). This may be done in any suitable manner. For example, in scenarios in which management facility 402 is implemented by computing system 302, computing system 302 may generate the stimulation program and load the stimulation program onto sound processor 104 (e.g., by transmitting data representative of the stimulation program to sound processor 104). Additionally or alternatively, computing system 302 may transmit data representative of the determined value for N to sound processor 104.

Once a stimulation program that utilizes the N-of-M channel selection strategy has been loaded onto sound processor 104, sound processor 104 may operate in accordance with the stimulation program. For example, sound processor 104 may divide an audio signal (e.g., sound presented to the user) into the M available analysis channels and select only the N analysis channels from the M available analysis channels for presentation to the user during the stimulation frame.

Figure 5:
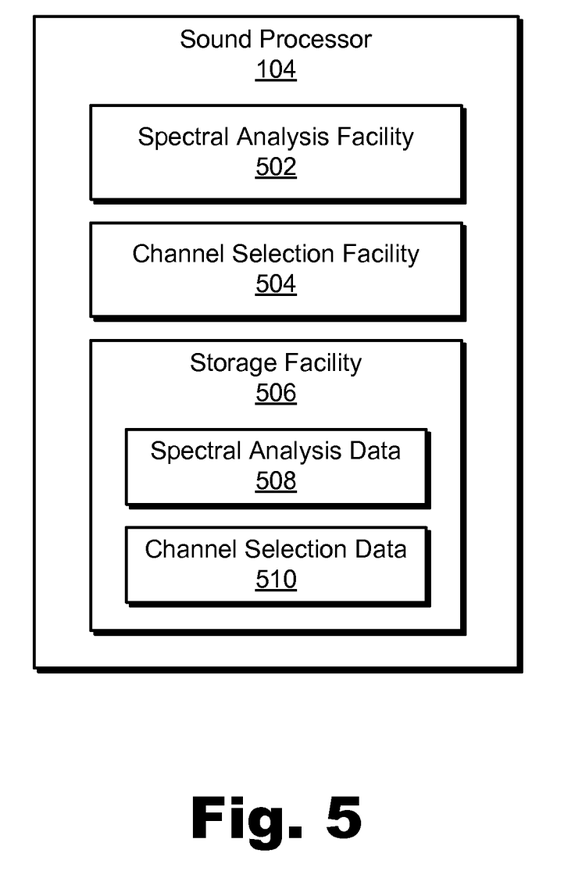
FIG. 5 illustrates exemplary components of a sound processor according to principles described herein.

To facilitate an understanding of how sound processor 104 may operate in accordance with a stimulation program that employs an N-of-M channel selection strategy, FIG. 5 illustrates exemplary components included in sound processor 104. As shown, sound processor 104 may include a spectral analysis facility 502, a channel selection facility 504, and a storage facility 506, which may be in communication with one another using any suitable communication technologies. Storage facility 506 may maintain spectral analysis data 508 generated and/or used by spectral analysis facility 502, and channel selection data 510 generated and/or used by channel selection facility 504. Storage facility 506 may maintain additional or alternative data as may serve a particular implementation. One or more of facilities 502-506 may include or be implemented one or more computing devices and/or processors configured to perform one or more of the functions described herein.

Spectral analysis facility 502 may divide an audio signal (e.g., an audio signal presented to the user and representative of speech and/or other types of sound) into M analysis channels. Each analysis channel includes a signal representative of a distinct portion of the audio signal. As used herein, "M" is an integer and refers to a total number of analysis channels into which an audio signal may be divided. For example, M may be any integer greater than three (e.g., equal to or greater than eight). In some examples, M is equal to the total number of stimulation channels formed by electrodes 112 through which electrical stimulation representative of the audio signal may be applied to the user.

Spectral analysis facility 502 may divide the audio signal into M analysis channels in any suitable manner. For example, spectral analysis facility 506 may be implemented by a plurality of band-pass filters configured to divide the audio signal into a plurality of frequency channels or bands. Additionally or alternatively, spectral analysis facility 506 may be configured to convert the audio signal from a time domain into a frequency domain and then divide the resulting frequency bins into the plurality of analysis channels. To this end, spectral analysis facility 502 may include one or more components configured to apply a Discrete Fourier Transform (e.g., a Fast Fourier Transform ("FFT")) to the audio signal.

Figure 6:
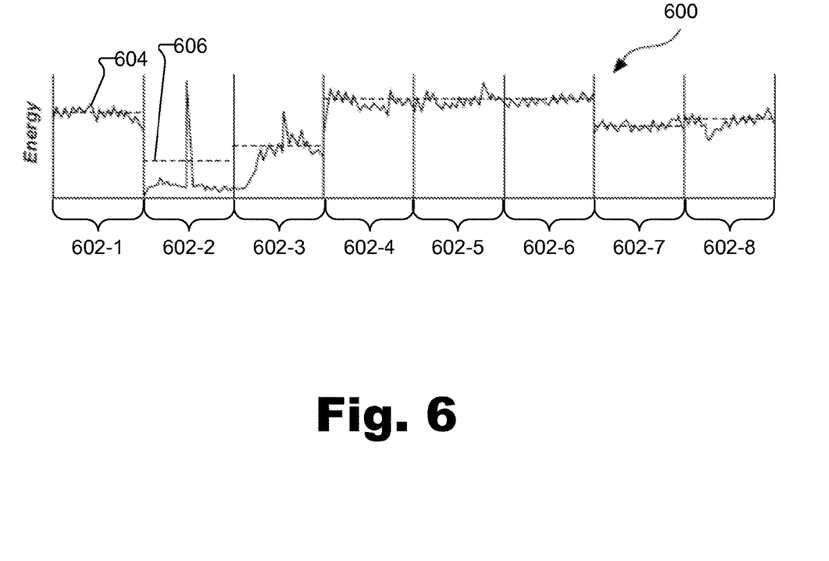
FIG. 6 illustrates an exemplary audio signal in the frequency domain that may be presented to a cochlear implant user according to principles described herein.

FIG. 6 illustrates an exemplary audio signal 600 in the frequency domain that may be presented to a cochlear implant user. As shown, the audio signal 600 may be divided by spectral analysis facility 502 into eight analysis channels 602 (e.g., analysis channels 602-1 through 602-8). In this case, M is equal to eight. It will be recognized that audio signal 600 may alternatively be divided into any other number of analysis channels as may serve a particular implementation.

Each analysis channel 602 may correspond to a distinct frequency band, and, as shown, includes a signal (e.g., signal 604) representative of a distinct portion of the audio signal. The vertical axis in FIG. 6 represents the amount of signal energy within each analysis channel 602. As shown in FIG. 6, each analysis channel contains varying energy levels. The average energy level in each analysis channel 602 is represented by a dashed horizontal line. For example, line 606 represents the average energy level included in analysis channel 602-2.

Returning to FIG. 5, channel selection facility 504 may select N analysis channels from the M total analysis channels for presentation to the user during a stimulation frame. As used herein, "N" is an integer greater than zero and less than or equal to M and refers to a total number of analysis channels that are selected for presentation to a user during a stimulation frame. For example, if M is equal to eight, N may be between one and eight. In some examples, N has to be less than M (e.g., in channel selection strategies in which it is desirable for only a subset of the M analysis channels to be selected for presentation to the user during a stimulation frame.

As used herein, an analysis channel that has been "selected for presentation" to a user during a stimulation frame refers to an analysis channel whose signal contained therein will be represented by electrical stimulation applied to the user during the stimulation frame. In other words, once an analysis channel has been selected for presentation to the user during the stimulation frame, sound processor 104 (e.g., channel selection facility 504) may direct cochlear implant 108 to apply electrical stimulation representative of the signal contained within the analysis channel to the user. For example, with reference again to FIG. 6, if analysis channel 602-1 is selected for presentation to the user during a stimulation frame, sound processor 104 may direct cochlear implant 108 to apply electrical stimulation representative of signal 604 to the user during the stimulation frame.

As used herein, a "stimulation frame" refers to a period of time during which electrical stimulation representative of the N selected analysis channels is applied to one or more stimulation channels defined by one or more of electrodes 112. During a stimulation session, a plurality of stimulation frames may temporally follow one another. For example, a first stimulation frame, a second stimulation frame, a third stimulation frame, etc. may follow sequentially right after one another as an audio signal is represented to a cochlear implant user.

Channel selection facility 504 may select the N analysis channels for presentation to the user in accordance with any suitable N-of-M channel selection strategy. For example, channel selection facility 504 may simply select the N analysis channels that contain the highest energy levels for presentation to the user. To illustrate, if N is equal to 6, channel selection facility 504 may select the four analysis channels with the highest energy levels for presentation to a user. In the example of FIG. 6, the four analysis channels with the highest average energy levels are channels 602-1, 602-4, 602-5, and 602-6. Hence, these analysis channels would be selected for presentation to the user. Other types of N-of-M channel selection strategies may additionally or alternatively be used in accordance with the systems and methods described herein.

Figure 7:
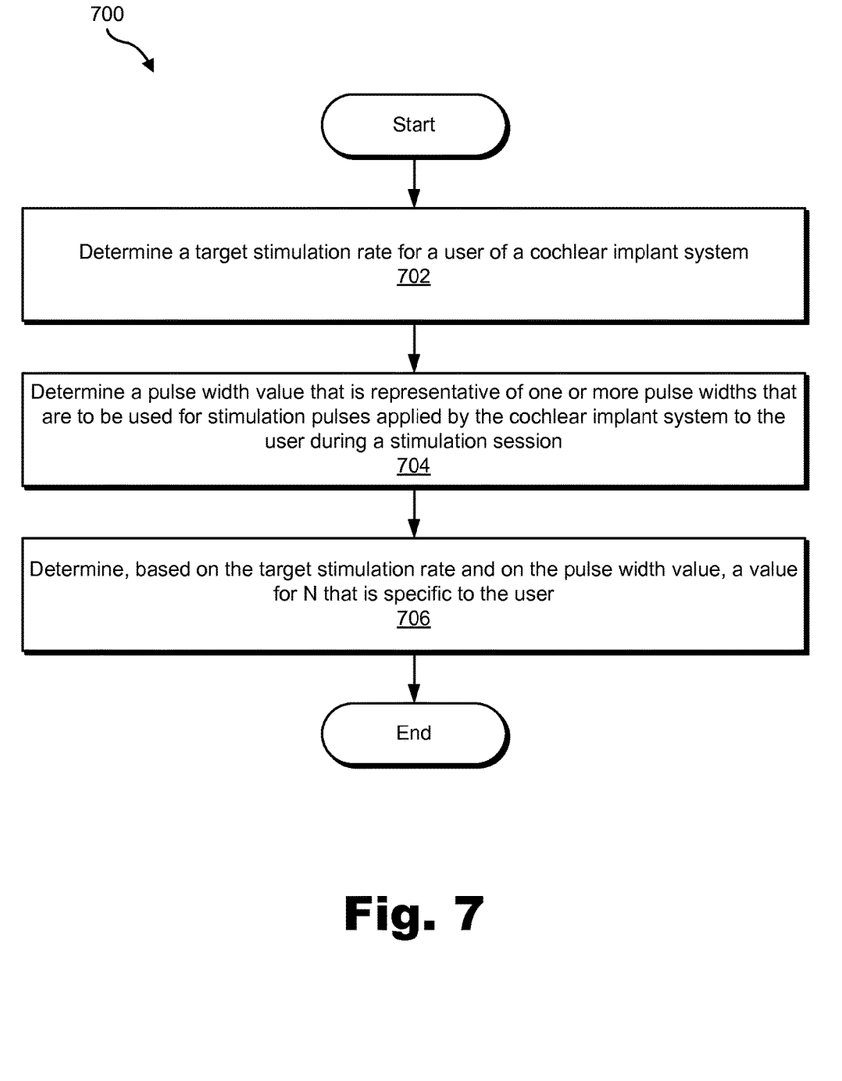
FIG. 7 illustrates an exemplary method according to principles described herein.

FIG. 7 illustrates an exemplary method 700. While FIG. 7 illustrates exemplary steps according to one embodiment, other embodiments may omit, add to, reorder, and/or modify any of the steps shown in FIG. 7. One or more of the steps shown in FIG. 7 may be performed by system 400 and/or any implementation thereof.

In step 702, a targeted channel selection system determines a target stimulation rate for a user of a cochlear implant system. Step 702 may be performed in any of the ways described herein.

In step 704, the targeted channel selection system determines a pulse width value that is representative of one or more pulse widths that are to be used for stimulation pulses applied by the cochlear implant system to the user during a stimulation session. Step 704 may be performed in any of the ways described herein.

In step 706, the targeted channel selection system determines, based on the target stimulation rate and on the pulse width value, a value for N that is specific to the user. Step 706 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer).

Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 8:
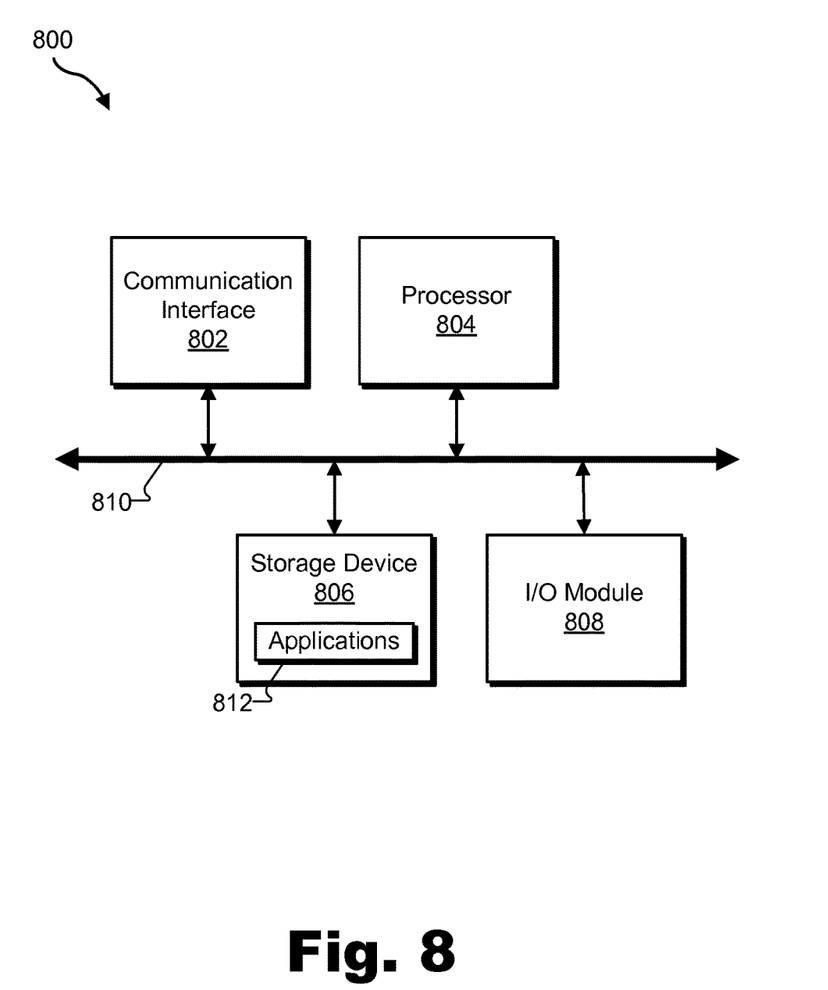
FIG. 8 illustrates an exemplary computing device according to principles described herein.

FIG. 8 illustrates an exemplary computing device 800 that may be configured to perform one or more of the processes described herein. As shown in FIG. 8, computing device 800 may include a communication interface 802, a processor 804, a storage device 806, and an input/output ("I/O") module 808 communicatively connected via a communication infrastructure 810. While an exemplary computing device 800 is shown in FIG. 8, the components illustrated in FIG. 8 are not intended to be limiting. Additional or alternative components may be used in other embodiments. Components of computing device 800 shown in FIG. 8 will now be described in additional detail.

Communication interface 802 may be configured to communicate with one or more computing devices. Examples of communication interface 802 include, without limitation, a wired network interface (such as a network interface card), a wireless network interface (such as a wireless network interface card), a modem, an audio/video connection, and any other suitable interface.

Processor 804 generally represents any type or form of processing unit capable of processing data or interpreting, executing, and/or directing execution of one or more of the instructions, processes, and/or operations described herein. Processor 804 may direct execution of operations in accordance with one or more applications 812 or other computer-executable instructions such as may be stored in storage device 806 or another computer-readable medium.

Storage device 806 may include one or more data storage media, devices, or configurations and may employ any type, form, and combination of data storage media and/or device. For example, storage device 806 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 806. For example, data representative of one or more executable applications 812 configured to direct processor 804 to perform any of the operations described herein may be stored within storage device 806. In some examples, data may be arranged in one or more databases residing within storage device 806.

I/O module 808 may be configured to receive user input and provide user output and may include any hardware, firmware, software, or combination thereof supportive of input and output capabilities. For example, I/O module 808 may include hardware and/or software for capturing user input, including, but not limited to, a keyboard or keypad, a touch screen component (e.g., touch screen display), a receiver (e.g., an RF or infrared receiver), and/or one or more input buttons.

I/O module 808 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 808 is configured to provide graphical data to a display for presentation to a user. The graphical data may be representative of one or more graphical user interfaces and/or any other graphical content as may serve a particular implementation.

In some examples, any of the facilities and/or systems described herein may be implemented by or within one or more components of computing device 800. For example, one or more applications 812 residing within storage device 806 may be configured to direct processor 804 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   at least one processing device that
      determines a target stimulation rate for a user of a cochlear implant system,
      determines a pulse width value that is representative of one or more pulse widths that are to be used for stimulation pulses applied by the cochlear implant system to the user during a stimulation session, and
      determines, based on the target stimulation rate and on the pulse width value, a value for N that is specific to the user;
   wherein N represents a total number of analysis channels that are to be selected from M available analysis channels for presentation by the cochlear implant system to the user during a stimulation frame of the stimulation session and wherein N is less or equal to than M.

2. The system of claim 1, wherein the at least one processing device determines the target stimulation rate by receiving user input representative of the target stimulation rate.

3. The system of claim 1, wherein the at least one processing device determines the target stimulation rate by:
   identifying a stimulation rate used in a non-channel selection stimulation program for the user; and
   designating the identified stimulation rate as the target stimulation rate.

4. The system of claim 1, wherein the at least one processing device determines the target stimulation rate by:
   identifying a stimulation program that the user prefers;
   identifying a stimulation rate used in the identified stimulation program; and
   designating the identified stimulation rate as the target stimulation rate.

5. The system of claim 1, wherein the at least one processing device determines the target stimulation rate by:
   using a plurality of different stimulation rates during a fitting session for the user;
   obtaining feedback from the user with respect to the different stimulation rates; and
   designating, based on the feedback, a particular stimulation rate included in the plurality of different stimulation rates as the target stimulation rate.

6. The system of claim 1, wherein the at least one processing device determines the pulse width value by receiving user input representative of the pulse width value.

7. The system of claim 1, wherein the at least one processing device determines the pulse width value based on a most comfortable loudness level associated with the user and a power consumption requirement associated with the cochlear implant system.

8. The system of claim 1, wherein the pulse width value represents an average pulse width of the one or more pulse widths.

9. The system of claim 1, wherein the at least one processing device determines the value for N in accordance with $N_{value}=1/(PW*Rate_{target})$, wherein $N_{value}$ represents the value for N, PW represents the pulse width value, and $Rate_{target}$ represents the target stimulation rate.

10. The system of claim 1, wherein the at least one processing device determines the value for N in accordance with $N_{value}=\max(N_{min}, 1/(PW*Rate_{target}))$, wherein $N_{value}$ represents the value for N, $N_{min}$ represents a predetermined minimum value for N, PW represents the pulse width value, and $Rate_{target}$ represents the target stimulation rate.

11. The system of claim 1, wherein the at least one processing device generates a stimulation program that directs the cochlear implant system to select only the N analysis channels from the M available analysis channels for presentation to the user during the stimulation frame while the cochlear implant system operates in accordance with the stimulation program.

12. The system of claim 1, wherein the at least one processing device is at least partially implemented by a sound processor included in the cochlear implant system.

13. The system of claim 12, wherein the sound processor:
   divides an audio signal into the M available analysis channels; and
   selects only the N analysis channels from the M available analysis channels for presentation to the user during the stimulation frame.

14. The system of claim 1, wherein the at least one processing device is at least partially implemented by a computing system separate from the cochlear implant system.

15. The system of claim 14, wherein the computing system transmits data representative of the determined value for N to the cochlear implant system.

16. The system of claim 1, wherein N is less than M.

17. A system comprising:
   a computing system that selectively couples to a sound processor included in a cochlear implant system associated with a user and that
      determines a target stimulation rate for the user,
      determines a pulse width value that is representative of one or more pulse widths that are to be used for stimulation pulses applied by the cochlear implant system to the user during a stimulation session,
      determines, based on the target stimulation rate and on the pulse width value, a value for N that is specific to the user, wherein N represents a total number of analysis channels that are to be selected from M available analysis channels for presentation by the cochlear implant system to the user during a stimulation frame of the stimulation session and wherein N is less than M,
      generates a stimulation program that utilizes an N-of-M channel selection strategy based on the determined value for N, and
      transmits data representative of the stimulation program to the sound processor while the computing system is selectively coupled to the sound processor.

18. The system of claim 17, wherein the computing system determines the value for N in accordance with $N_{value}=1/(PW*Rate_{target})$, wherein $N_{value}$ represents the value for N, PW represents the pulse width value, and $Rate_{target}$ represents the target stimulation rate.

19. The system of claim 17, wherein the computing system determines the value for N in accordance with $N_{value}=\max(N_{min}, 1/(PW*Rate_{target}))$, wherein $N_{value}$ represents the value for N, $N_{min}$ represents a predetermined minimum value for N, PW represents the pulse width value, and $Rate_{target}$ represents the target stimulation rate.

20. A method comprising:
   determining, by a targeted channel selection system, a target stimulation rate for a user of a cochlear implant system;
   determining, by the targeted channel selection system, a pulse width value that is representative of one or more pulse widths that are to be used for stimulation pulses applied by the cochlear implant system to the user during a stimulation session; and
   determining, by the targeted channel selection system based on the target stimulation rate and on the pulse width value, a value for N that is specific to the user;
   wherein N represents a total number of analysis channels that are to be selected from M available analysis channels for presentation by the cochlear implant system to the user during a stimulation frame of the stimulation session and wherein N is less than M.

* * * * *